United States Patent
Huang et al.

(10) Patent No.: US 9,034,864 B2
(45) Date of Patent: May 19, 2015

(54) AZETIDINYLOXYPHENYLPYRROLIDINE COMPOUNDS

(71) Applicant: Eli Lilly and Company, Indianapolis, IN (US)

(72) Inventors: Danwen Huang, Bellevue, WA (US); Joshua O Odingo, Bothell, WA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/200,376

(22) Filed: Mar. 7, 2014

(65) Prior Publication Data

US 2014/0275002 A1    Sep. 18, 2014

Related U.S. Application Data

(60) Provisional application No. 61/778,546, filed on Mar. 13, 2013.

(51) Int. Cl.
| | |
|---|---|
| *A61K 31/00* | (2006.01) |
| *C07D 401/00* | (2006.01) |
| *C07D 401/14* | (2006.01) |
| *A61K 31/4439* | (2006.01) |
| *A61K 31/4985* | (2006.01) |

(52) U.S. Cl.
CPC .......... *C07D 401/14* (2013.01); *A61K 31/4439* (2013.01); *A61K 31/4985* (2013.01)

(58) Field of Classification Search
None
See application file for complete search history.

(56) References Cited

FOREIGN PATENT DOCUMENTS

| WO | 01/47905 A1 | 7/2001 |
|---|---|---|
| WO | WO 2001/047905 A1 * | 7/2001 |
| WO | 2007/039075 A2 | 4/2007 |

OTHER PUBLICATIONS

Yasuhiro Kaiho, et al., "The effects of a type 4 phosphodiesterase inhibitor and the muscarinic cholinergic antagonist tolterodine tartrate on detrusor overactivity in female rats with bladder outlet obstruction" Journal Compilation, 2007 BJU International, 101, 615-620.

Paul J Nichols, et al., "Preparation of Pyrrolidine-Based PDE4 Inhibitors via Enantioselective Conjugate Addition of a-Substituted Malonates to Aromatic Nitroalkenes" Organic Letters, 2006, vol. 8, No. 7, 1495-1498.

* cited by examiner

*Primary Examiner* — Rita Desai
*Assistant Examiner* — Ben S Michelson
(74) *Attorney, Agent, or Firm* — Mark A. Winter

(57) ABSTRACT

The invention provides certain azetidinyloxyphenylpyrrolidine compounds, particularly compounds of formula I wherein R is hydrogen or methyl, and pharmaceutical compositions thereof. The invention further provides methods of using a compound of formula I to treat overactive bladder.

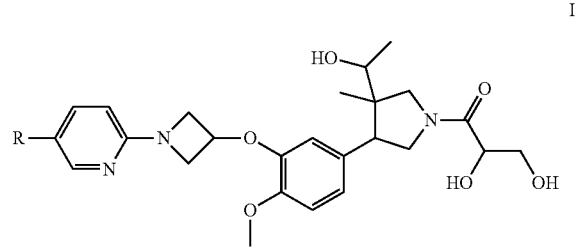

6 Claims, No Drawings

AZETIDINYLOXYPHENYLPYRROLIDINE COMPOUNDS

The invention provides certain azetidinyloxyphenylpyrrolidine compounds, pharmaceutical compositions thereof, methods of using the same, and processes for preparing the same.

Overactive bladder (OAB) is a symptomatically defined medical condition referring to the symptoms of urinary frequency and urgency, with or without urge incontinence. OAB is a condition that adversely affects the quality of life and social functioning of approximately 17 percent of the adult population. In spite of progress made for OAB treatment, many patients suffer with OAB for years without resolution. The first-line treatment for OAB are antimuscarinic drugs which have a good initial response, but experience diminishing patient compliance over the long term due to adverse effects and decreasing efficacy. There remains a significant unmet need for safe and effective OAB treatments.

Cyclic nucleotides (cAMP and cGMP) are important secondary messengers that modulate the contractility of smooth muscle. Cyclic nucleotide phosphodiesterases (PDEs) hydrolyse cyclic nucleotides and are important in regulating the level and duration of action of cyclic nucleotides inside cells. Compounds which inhibit PDE elevate cellular levels of cyclic nucleotides and thereby relax many types of smooth muscle. Previous studies have shown that relaxation of bladder smooth muscle is mainly mediated by agents that elevate cAMP. Phosphodiesterase 4 (PDE4) is cAMP specific and abundantly expressed in bladder. As such, PDE4 has been implicated in the control of bladder smooth muscle tone in vitro and in animal models of overactive bladder (Kaiho, Y. et al. *BJU International* 2008, 101(5), 615-620).

The compounds of the present invention are inhibitors of phosphodiesterase 4 (PDE4) and demonstrate selectivity for PDE4. As such, compounds of the present invention are believed to be useful for the treatment of conditions in which PDE4 plays a role such as overactive bladder, including relief of associated symptoms such as frequency and urgency.

International Application Publication WO 01/47905 discloses certain pyrrolindine derivative compounds as inhibitors of phosphodiesterase, in particular, PDE4, and recites the compounds as useful in treating a number of diseases including asthma.

The present invention provides novel compounds which are inhibitors of PDE4 and as such, are useful in treatment of overactive bladder and other disorders. The compounds provided address the need for safe and effective treatments of conditions associated with PDE4 such as overactive bladder.

The present invention provides a compound of formula I

I

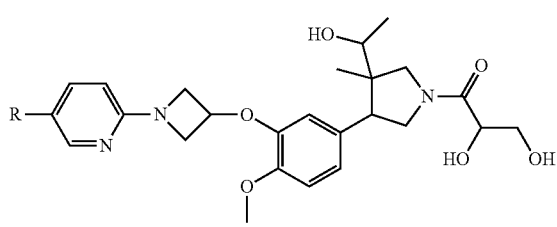

wherein R is hydrogen or methyl, or a pharmaceutically acceptable salt thereof.

A particular compound of formula I is one wherein R is methyl or a pharmaceutically acceptable salt thereof.

A particular compound of formula I is (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, or a pharmaceutically acceptable salt thereof.

Further, the present invention provides a pharmaceutical composition comprising a compound of formula I, or a pharmaceutically acceptable salt thereof, and a pharmaceutically acceptable carrier, diluent or excipient. In a particular embodiment, the pharmaceutical composition further comprises one or more other therapeutic agents such as tadalafil. As such, the present invention provides a pharmaceutical composition comprising a first component which is a compound of formula I, or a pharmaceutically acceptable salt thereof, and a second component which is tadalafil, and a pharmaceutically acceptable carrier, diluent or excipient.

Further, the present invention provides a compound of formula I, or a pharmaceutically acceptable salt thereof, for use in therapy.

Further, the present invention provides a compound of formula I, or a pharmaceutically acceptable salt thereof, for use in the treatment of overactive bladder.

Further, the present invention provides the use of a compound of formula I, or a pharmaceutically acceptable salt thereof, for the manufacture of a medicament for treating overactive bladder.

A particular compound of formula I is a compound of formula Ia

Ia

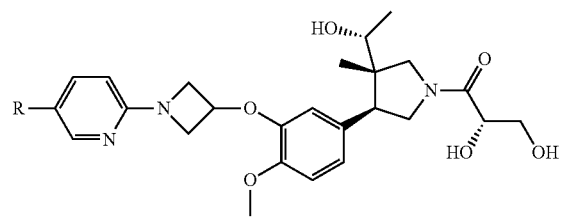

wherein R is hydrogen or methyl, or a pharmaceutically acceptable salt thereof.

A particular compound of formula Ia is one wherein R is methyl, or a pharmaceutically acceptable salt thereof.

A particular compound of formula Ia is (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, or a pharmaceutically acceptable salt thereof.

Further, the present invention provides a method of treating overactive bladder, comprising administering to a patient in need thereof an effective amount of a compound of formula Ia, or a pharmaceutically acceptable salt thereof. In a particular embodiment, the invention provides a method of treating overactive bladder, comprising administering to a patient in need thereof an effective amount of a first component which is a compound of formula Ia, or a pharmaceutically acceptable salt thereof, in combination with an effective amount of a second component which is tadalafil.

Further, the invention provides a method of treating overactive bladder comprising administrating to a patient in need thereof an effective amount of (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol, or a pharmaceutically acceptable salt thereof, in combination with an effective amount of tadalafil.

It is understood that compounds of the present invention may exist as stereoisomers. Embodiments of the present invention include all enantiomers, diastereomers, and mixtures thereof. Preferred embodiments are single diastereomers, and more preferred embodiments are single enantiomers.

The term "pharmaceutically acceptable salt" includes an acid addition salt that exists in conjunction with the basic portion of a compound of formula I. Such salts include the pharmaceutically acceptable salts, for example those listed in Handbook of Pharmaceutical Salts: Properties, Selection and Use, P. H. Stahl and C. G. Wermuth (Eds.), Wiley-VCH, New York, 2002 which are known to the skilled artisan.

In addition to pharmaceutically acceptable salts, other salts are contemplated in the invention. They may serve as intermediates in the purification of compounds or in the preparation of other pharmaceutically-acceptable salts, or are useful for identification, characterization or purification of compounds of the invention.

As used herein, the term "patient" refers to a warm blooded animal such as a mammal and includes a human. A human is a preferred patient.

It is also recognized that one skilled in the art may treat overactive bladder by administering to a patient presently displaying symptoms an effective amount of the compound of formula I. Thus, the terms "treatment" and "treating" are intended to refer to all processes wherein there may be a slowing, interrupting, arresting, controlling, or stopping of the progression of an existing disorder and/or symptoms thereof, but does not necessarily indicate a total elimination of all symptoms.

It is also recognized that one skilled in the art may treat overactive bladder by administering to a patient at risk of future symptoms an effective amount of the compound of formula I and is intended to include prophylactic treatment of such.

As used herein, the term "effective amount" of a compound of formula I refers to an amount, that is a dosage, which is effective in treating a disorder, such as overactive bladder described herein. The attending diagnostician, as one skilled in the art, can readily determine an effective amount by the use of conventional techniques and by observing results obtained under analogous circumstances. In determining an effective amount or dose of a compound of formula I, a number of factors are considered, including, but not limited to the compound of formula I to be administered; the co-administration of other agents, if used; the species of mammal; its size, age, and general health; the degree of involvement or the severity of the disorder, such as overactive bladder; the response of the individual patient; the mode of administration; the bioavailability characteristics of the preparation administered; the dose regimen selected; the use of other concomitant medication; and other relevant circumstances.

A compound of formula I may be used in combination with other drugs that are used in the treatment/prevention/suppression or amelioration of the diseases or conditions for which compounds of formula I are useful, including overactive bladder. Such other drug(s) may be administered by a route and in an amount commonly used therefore, including contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those containing one or more other active ingredients in addition to a compound of formula I. Other active ingredients effective in the treatment of overactive bladder which may be combined with a compound of formula I, either administered separately or in the same pharmaceutical include an inhibitor of PDE5 such as tadalafil.

The compounds of the present invention can be administered alone or in the form of a pharmaceutical composition combined with pharmaceutically acceptable carriers or excipients, the proportion, and nature of which are determined by the solubility and chemical properties, including stability, of the compound selected, the chosen route of administration, and standard pharmaceutical practice. The compounds of the present invention, while effective themselves, may also be formulated and administered in the form of their pharmaceutically acceptable salts for convenience of crystallization, increased solubility, and the like.

One skilled in the art of preparing formulations can readily select the proper form and mode of administration depending upon the particular characteristics of the compound selected, the disorder or condition to be treated, the stage of the disorder or condition, and other relevant circumstances (See, e.g., Remington: The Science and Practice of Pharmacy, D. B. Troy, Editor, 21st Edition., Lippincott, Williams & Wilkins, 2006).

PDE4 Inhibition In vitro Assay

The phosphodiesterase assays are performed essentially according to the method described in Loughney, K., et al., *J. Biol. Chem.*, 271, pp. 796-806 (1996). PDE4A, PDE4B, PDE4C, PDE4D, and PDE5 human recombinant proteins are expressed and purified from *Saccharomyes cerevisiae* that lack endogenous PDEs. The phosphodiesterase enzymes are diluted on ice with enzyme dilution buffer (25 mM Tris, pH 7.5, 0.1 mM DTT, 5.0 mM $MgCl_2$, 100 mM NaCl, 5 µM $ZnSO_4$, 100 µg/mL BSA) to give approximately 20%-40% hydrolysis of cyclic nucleotide monophosphate (cNMP) in the absence of inhibitor.

The stock solution of test compounds are diluted on the Beckman BioMek™ 1000 workstation to span a concentration range of 4.5 log units in 0.5 log increments. The DMSO concentration in the final test system is 2.5% for all PDE enzymes. The final test compound concentration tested ranged from 0.03 nM to 1 µM.

The assay is performed in a 96-well microtiter plate format on a Beckman BioMek™ 1000 robotic station. Each row of the plate represents a 10-point dose response curve containing blank (no enzyme), non-inhibited control, and inhibitor dilutions spanning 4.5 log units in concentration in 0.5 log increments. Assay stock solutions are loaded into the Biomek reservoirs (water, inhibitor diluent [2.5% or 10% DMSO], 5×PDE assay buffer, substrate, inhibitor solutions, enzyme solutions, snake venom nucleotidase, and charcoal suspension). The reaction is initiated with enzyme, and incubated for 15 minutes at 30° C. An excess of *Crotalus atrox* snake venom nucleotidase (5 µL/well) is then added and the mixture is incubated for an additional 3 minutes. The reaction is terminated by the addition of 200 µL of activated charcoal suspension, after which the plate is centrifuged for 5 minutes at 750×g. A transfer program is run in which 200 µL of supernatant is removed and placed into a new plate. The amount of radioactivity released as phosphate is determined in a Wallac MicroBeta Plate™ counter.

The reduced data at each concentration of inhibitor is analyzed using a four-, three- or two-parameter logistic dose response model to provide an $IC_{50}$ value. For those sets of data that exhibited >95% inhibition at the maximal inhibitor concentration, a four-parameter logistic dose response model is used.

In the above assay, the compounds Examples 1 and 2 exhibit an $IC_{50}$ of less than 10 nM at PDE4B. More specifically, the compound of Example 2 has an $IC_{50}$ of 0.58 nM measured at PDE4B in the above assay. These data demonstrate the compounds of Example 1 and 2 are inhibitors of PDE4B.

Overactive Bladder In vivo Model

The in vivo effect of PDE4 inhibitors on OAB is studied with a chronic cyclophosphamide (CYP)-induced overactive bladder mouse model adapted from Boudes et al., *Neurourol. Urodynam.* 2011. In a typical study, female C57/B16 mice, approximately 20 grams in body weight (Harlan Laboratories, Inc., Indianapolis, Ind.) are used. Mice are randomized by body weight into groups one day before the start of the study. Mice are individually housed and maintained on a 12 hour light/dark cycle at 22° C. with ad lib access to food (TD 2014 with 0.72% Ca and 0.61% P, 990 IU/g D3, Teklad™, Madison, Wis.) and water Animals receive cyclophosphamide (dissolved in physiological saline) i.p. administration at 100 mg/kg on days 1, 3, 5, and 7 to chronically induce OAB. The vehicle control group received daily vehicle (HEC 1%/Tween 80 0.25%/Antifoam 0.05%) administered orally. All other groups are administered orally tadalafil at 10 mg/kg in combination with 0.1, 1.0, or 10.0 mg/kg of test compound daily at a volume of 200 μl/mouse. On day 8, mice are housed in urine collection chambers with a filter paper placed underneath chamber. Prior to urine collection, gavages of 1 ml water are given to each mouse. Urine is collected from 6 μm to 10 μm (i.e. for 4 hrs). Gel cups (DietGel™ 76A) are supplied as water source during the 4 hour period. The filter paper is changed every hour. Voiding frequency and volume/void are calculated using Image J software (NIH). Data are statistically analyzed with JMP8® software (Cary, N.C.).

The animals develop OAB after 8 days following CYP treatment as demonstrated by increased urinary frequency (sham: 6.66±0.91 vs. vehicle: 16.5±1.65 number of urination/4 hour period) and decreased volume/void (sham: 173.36±38.39 mL vs. vehicle: 31.93±4.16 mL). All treatment groups receive a fixed dose of 10 mg/kg of tadalafil. At this dose, tadalafil has no significant activity on either urinary frequency or volume per void. Following the protocol essentially as described above, the compound of Example 2 given with tadalafil significantly reduces urinary frequency in a dose-dependent fashion (Table 1). In addition, increases of volume/void are also observed in a dose-dependent fashion (Table 2). This demonstrates that a compound of Example 2 in combination with tadalafil is active in an animal model of overactive bladder.

TABLE 1

| Treatment | Mean Voiding Frequency (no./4 hr) | Standard Error | p value vs. Vehicle* |
|---|---|---|---|
| Vehicle | 16.5 | 1.6583 | |
| Example 2 0.1 mg/kg + tadalafil 10 mg/kg | 10 | 0.9587 | 0.0057 |
| Example 2 1.0 mg/kg + tadalafil 10 mg/kg | 8.61 | 0.7633 | 0.0003 |

TABLE 1-continued

| Treatment | Mean Voiding Frequency (no./4 hr) | Standard Error | p value vs. Vehicle* |
|---|---|---|---|
| Example 2 10.0 mg/kg + tadalafil 10 mg/kg | 8.38 | 1.2049 | 0.0000 |

*p < 0.05 is statistically significant; p < 0.001 is statistically highly significant; p-values computed based on ANOVA model for the square root transform of number of spots in 4 hours; p-values adjusted for multiple comparisons to vehicle using Dunnett's correction.

TABLE 2

| Treatment | Mean Volume/Void (mL) | Standard Error | p value vs. Vehicle* |
|---|---|---|---|
| Vehicle | 31.93 | 4.1635 | |
| Example 2 0.1 mg/kg + tadalafil 10 mg/kg | 47.30 | 6.3428 | 0.29619 |
| Example 2 1.0 mg/kg + tadalafil 10 mg/kg | 77.15 | 5.6815 | 0.00003 |
| Example 2 10.0 mg/kg + tadalafil 10 mg/kg | 81.93 | 10.0205 | 0.00007 |

*p < 0.05 is statistically significant; p < 0.001 is statistically highly significant; p-values computed based on ANOVA model for the logarithm of urine spot volumes; p-values adjusted for multiple comparisons to vehicle using Dunnett's correction.

Compounds of formula I may be prepared by processes known in the chemical art for the production of structurally analogous compounds or by a novel process described herein. A process for the preparation of a compound of formula I, or a pharmaceutically acceptable salt thereof, and novel intermediates for the manufacture of a compound of formula I, provide further features of the invention and are illustrated by the following procedures in which the meaning of substituent, R is as defined above, unless otherwise specified.

Generally, a compound of formula Ia where R is hydrogen or methyl may be prepared from a compound of formula II where the 1,2-diol group is protected with a suitable group such as acetonide (Scheme 1). More specifically, a compound of formula II is reacted with an acid such aqueous hydrochloric acid or acetic acid in a suitable solvent to provide a compound of formula Ia. Suitable solvents include water, methanol and acetonitrile. A compound of formula II where R is hydrogen or methyl may be prepared by reacting a compound of formula III with a compound of formula IV where L represents a suitable leaving group such as fluoro or chloro in the presence of a suitable base. Suitable bases include potassium carbonate and cesium carbonate. The reaction is conveniently carried out in a solvent such as N-methyl-2-pyrrolidone or acetonitrile.

A compound of formula III may be prepared from a compound of formula V where the azetidine amine is protected with a suitable group such as diphenylmethyl. More specifically, a compound of formula V is reacted with hydrogen gas in the presence of suitable catalyst such as palladium on carbon to provide a compound of formula III. The reaction is conveniently carried out in a solvent such as methanol or ethanol.

A compound of formula V may be prepared by reacting a compound of formula VI with 1-(diphenylmethyl)azetidin-3-yl methanesulfonate in the presence of a suitable base. Suitable bases include potassium carbonate and cesium carbonate. The reaction is conveniently carried out in an appropriate solvent such as acetonitirile.

Scheme 1

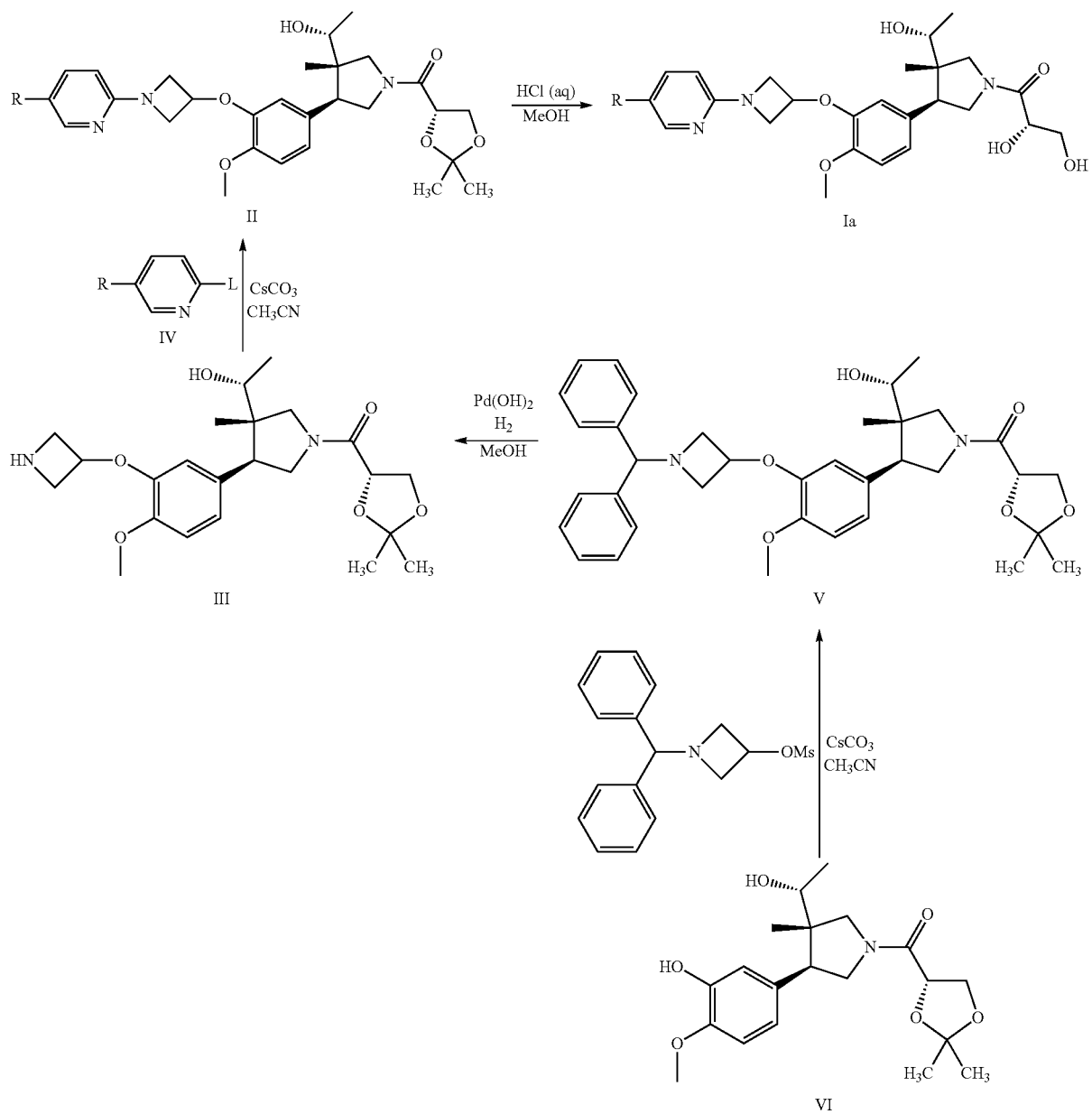

Alternatively, a compound of formula II may be prepared directly from a compound of formula VI (Scheme 2). More specifically, a compound of formula VI is reacted with a compound of formula VII where R is hydrogen or methyl and OMs represents the leaving group methanesulfonyl in the presence of a suitable base such as cesium carbonate. The reaction is conveniently carried out in an appropriate solvent such as acetonitirile.

A compound of formula VII may be prepared by reacting a compound of formula VIII with methanesulfonyl chloride in the presence of a base such as triethylamine. The reaction is conveniently carried out in a suitable solvent such as methylene chloride. A compound of formula VIII where R is hydrogen or methyl may be prepared by reacting a compound of formula IV where L represents a suitable leaving group such as fluoro or chloro with 3-hydroxy azetidine in the presence of a suitable base. Suitable bases include potassium carbonate. The reaction is conveniently carried out in a suitable solvent.

Scheme 2

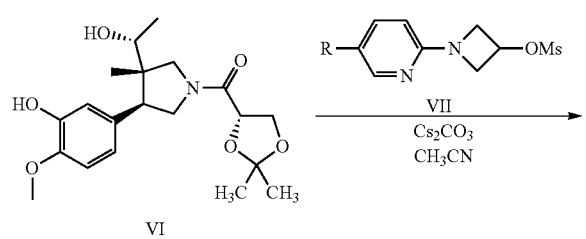

-continued

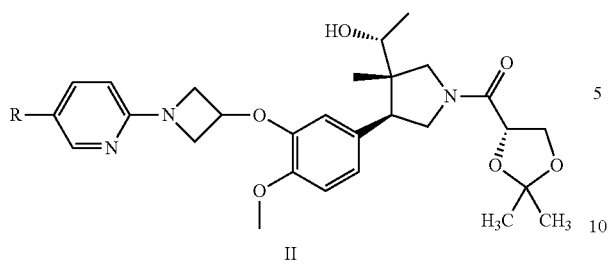

II

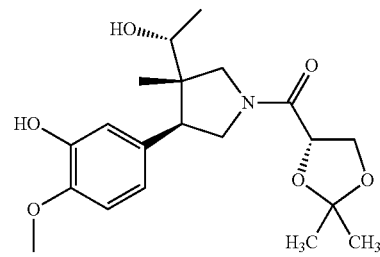

VI

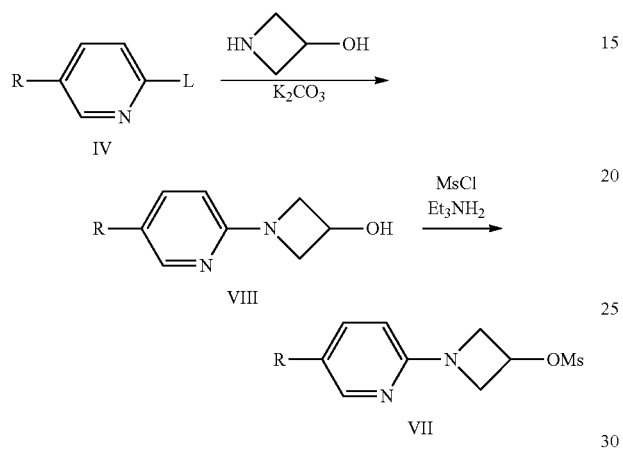

A compound of formula VI may be prepared by procedures appreciated by one of ordinary skill in the art including those disclosed in International Application Publication No. WO 01/47905 as well as those disclosed in Scheme 3 in view of Nichols, P. J.; DeMattei, J. A.; Barnett, B. R.; LeFur, N. A.; Chuang, T.; Piscopio, A. D.; Kock, K. *Org. Lett.* 2006, 8, 1495-1498.

Scheme 3

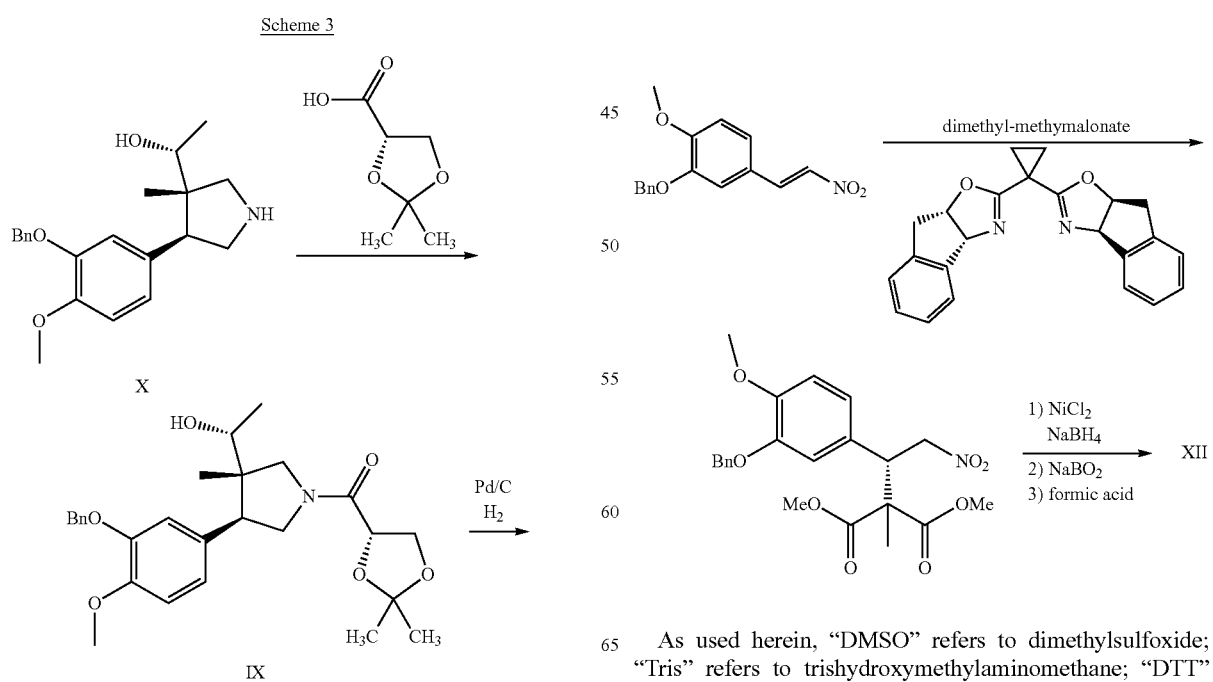

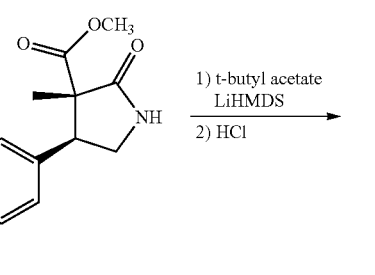

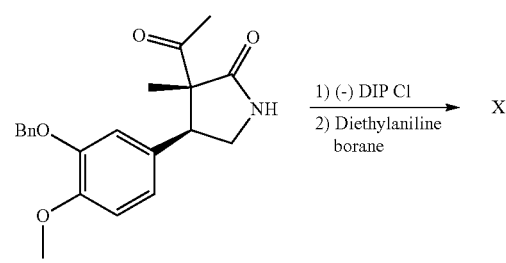

As used herein, "DMSO" refers to dimethylsulfoxide; "Tris" refers to trishydroxymethylaminomethane; "DTT" refers to dithiothreitol; "HEC" refers to hydroxyethyl cellulose; and "IC$_{50}$" refers to the concentration of an agent that produces 50% of the maximal inhibitory response possible for that agent.

Preparation 1

Synthesis of (1R)-1-[(3S,4S)-1-{[(4S)-2,2-dimethyl-1,3-dioxolan-4-yl]carbonyl}-4-(3-{[1-(diphenylmethyl)azetidin-3-yl]oxy}-4-methoxyphenyl)-3-methylpyrrolidin-3-yl]ethanol

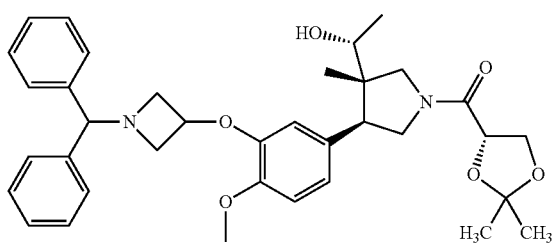 [SMILES: COc1ccc([C@@H]2CN(C(=O)[C@@H]3COC(C)(C)O3)C[C@@]2(C)[C@@H](C)O)cc1OC1CN(C(c2ccccc2)c2ccccc2)C1]

To a suspension of (1R)-1-[(3S,4S)-1-{[(4S)-2,2-dimethyl-1,3-dioxolan-4-yl]carbonyl}-4-(4-methoxy-3-hydroxyphenyl)-3-methylpyrrolidin-3-yl]ethanol (2.0 g) and potassium carbonate (1.46 g) in acetonitrile (30 mL) is added 1-(diphenylmethyl)azetidin-3-yl methanesulfonate (2.51 g). The mixture is heated at 80° C. overnight. Cool the reaction mixture and pour into ethyl acetate (100 mL), wash with water (40 mL) and brine (40 mL), dry over sodium sulfate, filter and evaporate the filtrate to dryness. Purify the resulting residue (silica gel, 60% ethyl acetate/hexanes to ethyl acetate) to provide 0.6 g of the title compound. MS (ES+)=601 (M+1).

Preparation 2

Synthesis of (1R)-1-[(3S,4S)-1-{[(4S)-2,2-dimethyl-1,3-dioxolan-4-yl]carbonyl}-4-(4-methoxy-3-{[1-(azetidin-3-yl]oxy}phenyl)-3-methylpyrrolidin-3-yl]ethanol

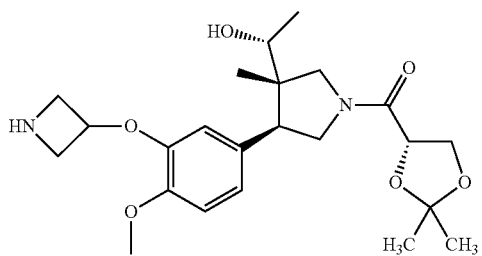 [SMILES: COc1ccc([C@@H]2CN(C(=O)[C@@H]3COC(C)(C)O3)C[C@@]2(C)[C@@H](C)O)cc1OC1CNC1]

To a Parr™ vessel containing a solution of (1R)-1-[(3S, 4S)-1-{[(4S)-2,2-dimethyl-1,3-dioxolan-4-yl]carbonyl}-4-(3-{[1-(diphenylmethyl)azetidin-3-yl]oxy}-4-methoxyphenyl)-3-methylpyrrolidin-3-yl]ethanol (0.6 g) in methanol (20 mL) is added palladium hydroxide on carbon (60 mg, 20 wt % Pd on C dry basis). The suspension is hydrogenated at 30 psig hydrogen gas until hydrogen gas uptake ceases. The reaction mixture is filtered through Celite™ and the filtrate is evaporated to provide the title compound (0.4 g). MS (ES+)=435 (M+1).

Preparation 3

Synthesis of (1R)-1-[(3S,4S)-1-{[(4S)-2,2-dimethyl-1,3-dioxolan-4-yl]carbonyl}-4-(4-methoxy-3-{[1-pyridin-2-ylazetidin-3-yl]oxy}phenyl)-3-methylpyrrolidin-3-yl]ethanol

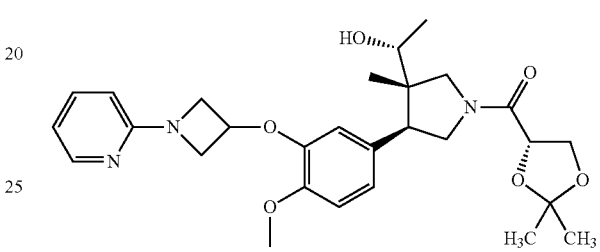

A mixture of (1R)-1-[(3S,4S)-1-{[(4S)-2,2-dimethyl-1,3-dioxolan-4-yl]carbonyl}-4-(4-methoxy-3-{[1-(azetidin-3-yl]oxy}phenyl)-3-methylpyrrolidin-3-yl]ethanol (50 mg), 2-fluoropyridine (11.8 mg) and potassium carbonate (31.8 mg) in N-methyl-2-pyrrolidone (3 mL) is heated at 120° C. overnight. The reaction is cooled, poured into methylene chloride (40 mL), and washed with water (10 mL). The organic layer is dried over sodium sulfate and evaporated to 3 mL. Acetonitrile is added and the crude product solution is purified by reverse phase chromatography (5% to 95% acetonitrile/water). The appropriate fractions are collected and evaporated to provide the title compound (22.1 mg). MS (ES+)=512 (M+1).

Preparation 4

Synthesis of (1R)-1-[(3S,4S)-1-{[(4S)-2,2-dimethyl-1,3-dioxolan-4-yl]carbonyl}-4-(4-methoxy-3-{[1(5-methylpyridin-2-yl)azetidin-3-yl]oxy}phenyl)-3-methylpyrrolidin-3-yl]ethanol

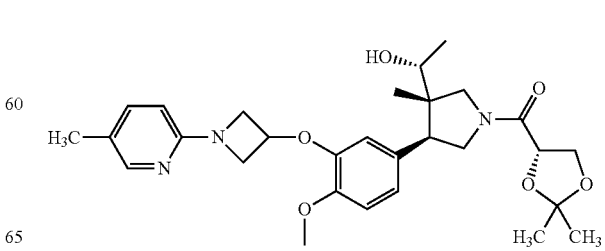

The title compound is prepared essentially by the method of Preparation 3 using 2-chloro-5-methylpyridine. MS(ES+) =526 (M+1).

EXAMPLE 1

Synthesis of (2S)-3-[(3S,4S)-3-[(1R)-1-hydroxyethyl]-4-{4-methoxy-3-[(1-pyridin-2-ylazetidin-3-yl)oxy]phenyl}-3-methylpyrrolidin-1-yl]-3-oxopropane-1,2-diol

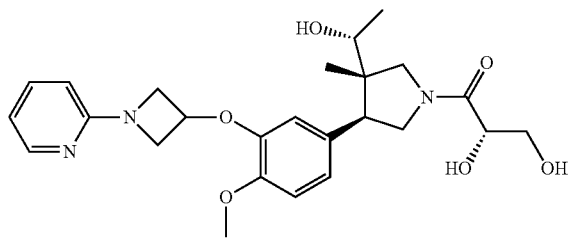 [SMILES: COc1ccc([C@@H]2CN(C(=O)[C@@H](O)CO)C[C@@]2(C)[C@@H](C)O)cc1OC1CN(c2ccccn2)C1]

To a solution of (1R)-1-[(3S,4S)-1-{[(4S)-2,2-dimethyl-1,3-dioxolan-4-yl]carbonyl}-4-(4-methoxy-3-{[1-pyridin-2-ylazetidin-3-yl]oxy}phenyl)-3-methylpyrrolidin-3-yl]ethanol (22.1 mg) in tetrahydrofuran (2 mL) is added aqueous 1.0 M HCl (1 mL). Stir overnight at room temperature. Add aqueous 1.0 M HCl (1 mL) and stir for additional 8 hours. Neutralize with aqueous 1.0 M NaOH, extract with ethyl acetate, dry and evaporate to provide the title compound (18.2 mg). MS(ES+)=472 (M+1).

EXAMPLE 2

Synthesis of (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol

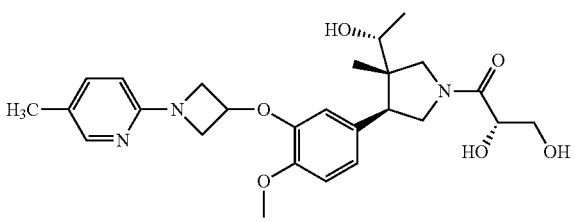 [SMILES: COc1ccc([C@@H]2CN(C(=O)[C@@H](O)CO)C[C@@]2(C)[C@@H](C)O)cc1OC1CN(c2ccc(C)cn2)C1]

The title compound is prepared essentially by the method of Example 1. MS(ES+)=486 (M+1).

We claim:

1. A compound of the formula

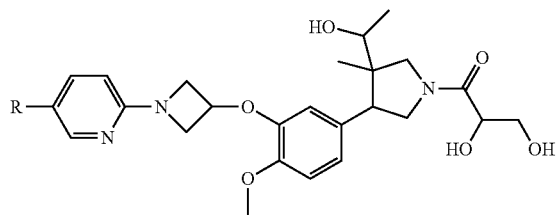

or a pharmaceutically acceptable salt thereof, wherein R is hydrogen or methyl.

2. The compound or salt of claim 1 of the formula

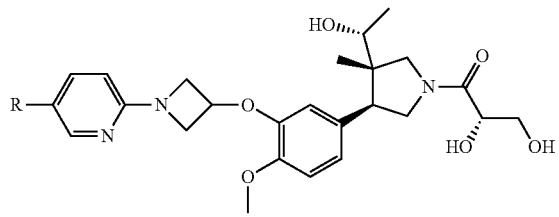

wherein R is hydrogen or methyl.

3. The compound or salt of claim 1 or 2 wherein R is methyl.

4. The compound which is (2S)-3-[(3S,4S)-3-[(1R)-1-hydroxyethyl]-4-(4-methoxy-3-{[1-(5-methylpyridin-2-yl)azetidin-3-yl]oxy}phenyl)-3-methylpyrrolidin-1-yl]-3-oxopropane-1,2-diol.

5. A pharmaceutical composition comprising a compound according to claim 1, or a pharmaceutically acceptable salt thereof, and a pharmaceutically acceptable carrier, diluent or excipient.

6. A method of treating overactive bladder comprising administrating to a patient in need thereof an effective amount of a compound according to claim 1, or a pharmaceutically acceptable salt thereof.

* * * * *